(12) United States Patent
Xiao

(10) Patent No.: US 7,806,917 B2  
(45) Date of Patent: Oct. 5, 2010

(54) STENT GRAFT FIXATION SYSTEM AND METHOD

(75) Inventor: Jia Hua Xiao, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 396 days.

(21) Appl. No.: 11/736,465

(22) Filed: Apr. 17, 2007

(65) Prior Publication Data

US 2008/0262596 A1    Oct. 23, 2008

(51) Int. Cl.  
*A61F 2/06* (2006.01)

(52) U.S. Cl. .................................. 623/1.13

(58) Field of Classification Search ............... None  
See application file for complete search history.

(56) References Cited

U.S. PATENT DOCUMENTS

| | | | |
|---|---|---|---|
| 5,617,878 A | 4/1997 | Taheri | |
| 5,693,086 A | 12/1997 | Goicoechea et al. | |
| 5,800,521 A | 9/1998 | Orth | |
| 5,906,619 A | 5/1999 | Olson et al. | |
| 5,948,017 A | 9/1999 | Taheri | |
| 5,989,263 A | 11/1999 | Shmulewitz | |
| 6,030,414 A | 2/2000 | Taheri | |
| 6,099,548 A * | 8/2000 | Taheri | 606/198 |
| 6,106,549 A | 8/2000 | Taheri | |
| 6,159,239 A * | 12/2000 | Greenhalgh | 623/1.13 |
| 6,253,768 B1 | 7/2001 | Wilk | |
| 6,287,315 B1 * | 9/2001 | Wijeratne et al. | 606/108 |
| 6,409,750 B1 | 6/2002 | Hyodoh et al. | |
| 6,723,116 B2 | 4/2004 | Taheri | |
| 6,960,217 B2 | 11/2005 | Bolduc | |
| 7,329,275 B2 * | 2/2008 | Yee | 623/1.11 |
| 2004/0236356 A1 | 11/2004 | Rioux et al. | |
| 2005/0015100 A1 * | 1/2005 | Parodi | 606/139 |
| 2005/0070924 A1 | 3/2005 | Schaller et al. | |
| 2005/0187613 A1 | 8/2005 | Bolduc et al. | |
| 2005/0288765 A1 | 12/2005 | Taheri | |
| 2006/0282088 A1 * | 12/2006 | Ryan | 606/144 |

\* cited by examiner

*Primary Examiner*—Kevin T Truong

(57) ABSTRACT

A stent graft fixation system and method including a stent graft for fastening to a fixation point in a body lumen, the stent graft including a stent; a graft material supported by the stent and having a fixation region; and a guide suture joined to the graft material in the fixation region. The guide suture has a length selected to extend from the fixation point to outside of the body lumen.

28 Claims, 17 Drawing Sheets

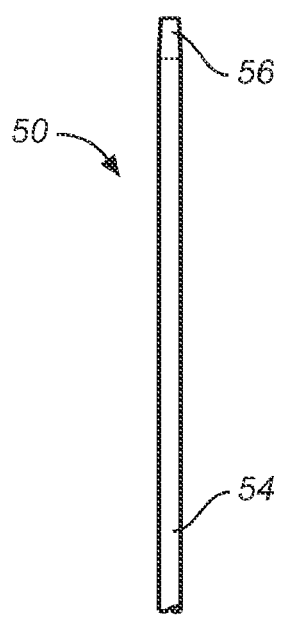
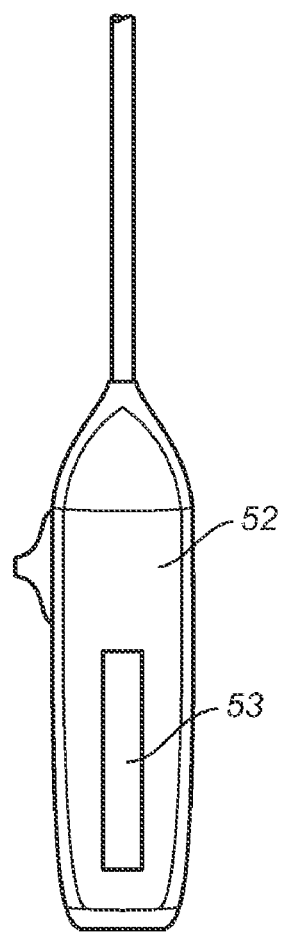
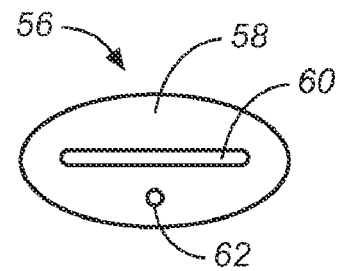
FIG. 5B
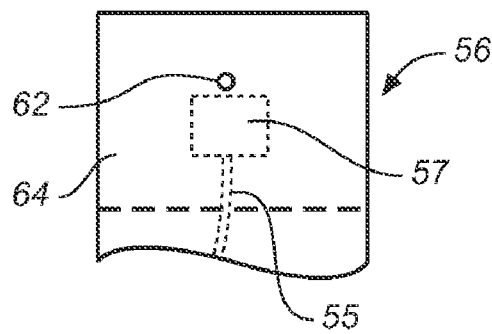
FIG. 5A  FIG. 5C

STENT GRAFT FIXATION SYSTEM AND METHOD

TECHNICAL FIELD

The technical field of this disclosure is medical implantation devices, particularly, a stent graft fixation system and method.

BACKGROUND OF THE INVENTION

Wide ranges of medical treatments have been developed using endoluminal prostheses, which are medical devices adapted for temporary or permanent implantation within a body lumen, such as naturally occurring or artificially made lumens. Examples of body lumens in which endoluminal prostheses may be implanted include arteries such as those located within coronary, mesentery, peripheral, or cerebral vasculature; veins; gastrointestinal tract; biliary tract; urethra; trachea; hepatic shunts; and fallopian tubes. Various types of endoluminal prostheses have also been developed with particular structure to modify the mechanics of the targeted luminal wall.

A number of vascular devices have been developed for replacing, supplementing, or excluding portions of blood vessels. These vascular devices include endoluminal vascular prostheses and stent grafts. Aneurysm exclusion devices, such as abdominal aortic aneurysm (AAA) devices, are used to exclude vascular aneurysms and provide a prosthetic lumen for the flow of blood. Vascular aneurysms are the result of abnormal dilation of a blood vessel, usually from disease or a genetic predisposition, which can weaken the arterial wall and allow it to expand. Aneurysms can occur in any blood vessel, but most occur in the aorta and peripheral arteries, with the majority of aneurysms occurring in the abdominal aorta. An abdominal aneurysm typically begins below the renal arteries and extends into one or both of the iliac arteries.

Aneurysms, especially abdominal aortic aneurysms, are commonly treated in open surgery procedures in which the diseased vessel segment is bypassed and repaired with an artificial vascular graft. While open surgery is an effective surgical technique in light of the risk of a fatal abdominal aortic aneurysm rupture, the open surgical technique suffers from a number of disadvantages. The surgical procedure is complex, requires a long hospital stay, requires a long recovery time, and has a high mortality rate. Less invasive devices and techniques have been developed to avoid these disadvantages. Tubular endoluminal prostheses that provide a lumen or lumens for blood flow while excluding blood flow to the aneurysm site are introduced into the blood vessel using a catheter in a less or minimally invasive technique. The tubular endoluminal prosthesis is introduced in a small diameter crimped condition and expanded at the aneurysm. Although often referred to as stent grafts, these tubular endoluminal prostheses differ from covered stents in that they are not used to mechanically prop open natural blood vessels. Rather, they are used to secure an artificial lumen in a sealing engagement with the vessel wall without further opening the abnormally dilated natural blood vessel.

Stent grafts for use in abdominal aortic aneurysms typically include a support structure supporting woven or interlocked graft material. Examples of woven graft materials are woven polymer materials, e.g., Dacron, or polytetrafluoroethylene (PTFE). Interlocked graft materials include knit, stretch, and velour materials. The graft material is secured to the inner or outer diameter of the support structure, which supports the graft material and/or holds it in place against a luminal wall. The stent graft is secured to a vessel wall above and below the aneurysm. A proximal spring stent of the stent graft can be located above the aneurysm to provide a radial force which engages the lumen wall and seals the stent graft at the lumen wall. The proximal spring stent can include hooks to puncture the vessel wall and further secure the stent graft in place.

One problem in present stent graft designs is the need to fix and/or seal the proximal end of the stent graft to the vessel wall. Fixing the stent graft to the vessel wall prevents inadvertent movement of the stent graft relative to the vessel wall. Sealing the stent graft to the vessel wall prevents fluid from bypassing the stent graft lumen and flowing between the graft material and the vessel wall. One proposed solution to this problem has been to use fasteners, such as staples or helical fasteners to attach the graft material to the vessel wall.

Unfortunately, it is difficult to accurately locate the fastener at the fixation point. X-rays can be used to view the relative location of the fastener to be installed and the fixation point, but the resolution is typically inadequate for accurate fastener placement. The fastener is small, on the order of 2-3 millimeters, and the projected image is planar, confusing the depth of the image. Contrast medium may further reduce image resolution through clouding.

It would be desirable to have a stent graft fixation system and method that would overcome the above disadvantages.

SUMMARY OF THE INVENTION

One aspect according to the present invention provides a stent graft for fastening to a fixation point in a body lumen, the stent graft including a stent; a graft material supported by the stent and having a fixation region; and a guide suture joined to the graft material in the fixation region, the guide suture having a length selected to extend from the fixation point to outside of the body lumen.

Another aspect according to the present invention provides a stent graft fixation system including a stent graft having graft material; a guide suture joined to the graft material; and a fixation tool having a fixation tool head, the fixation tool head defining a guide aperture operable to receive the guide suture.

Another aspect according to the present invention provides a method of fixing a stent graft to a body lumen wall, the method including providing a stent graft having graft material and a guide suture joined to the graft material; providing a fixation tool having a fixation tool head, the fixation tool head defining a guide aperture operable to receive the guide suture; deploying the stent graft in a body lumen; threading the guide suture through the guide aperture; guiding the fixation tool head along the guide suture to a fixation point; and fastening the graft material to the body lumen wall at the fixation point.

Another aspect according to the present invention provides a stent graft fixation system for stent graft fixation to a fixation point in a body lumen wall, the system including a stent graft having graft material and a guide suture joined to the graft material; means for fastening the graft material to the body lumen wall; means for delivering the fastening means along the guide suture to the fixation point; and means for deploying the fastening means at the fixation point.

BRIEF DESCRIPTION OF THE DRAWINGS

FIGS. 5A-5C are top, detailed front, and detailed bottom views, respectively, of a fixation tool for use with a stent graft in accordance with the present invention;

DETAILED DESCRIPTION

Figure 1A:
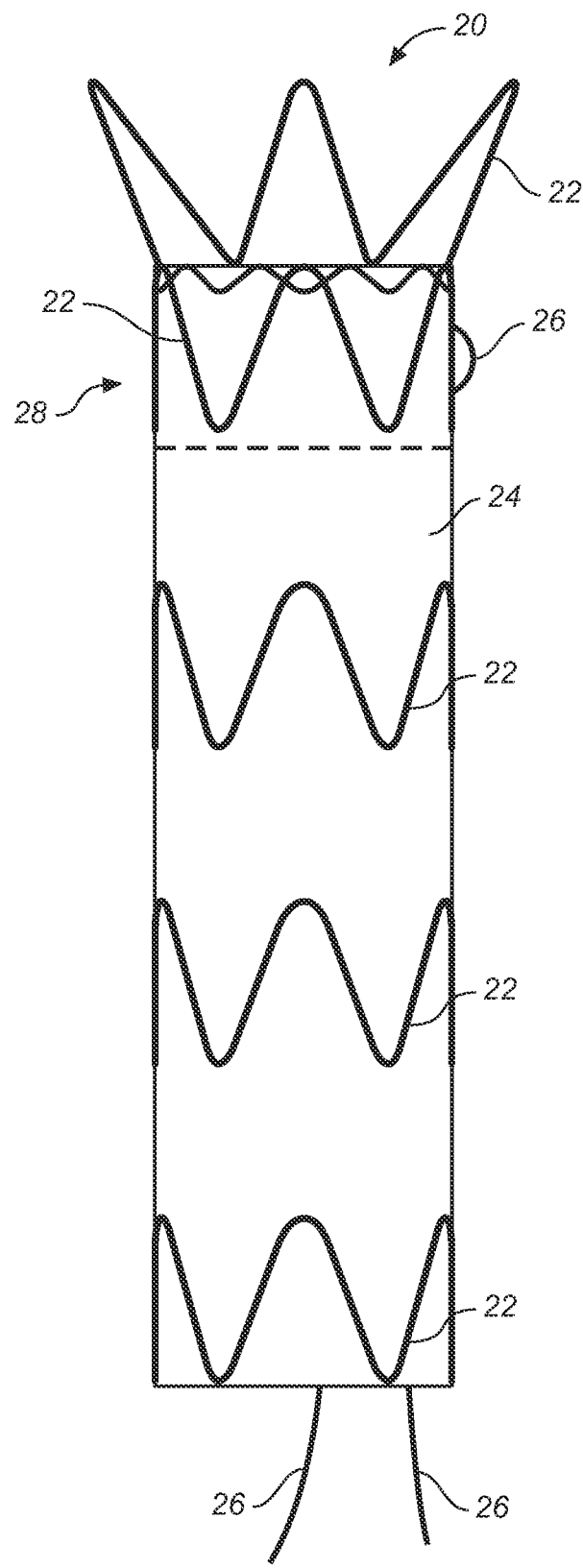
FIGS. 1A-1C are side, cross section, and detailed cross section views, respectively, of a stent graft in accordance with the present invention.
Figure 1B:
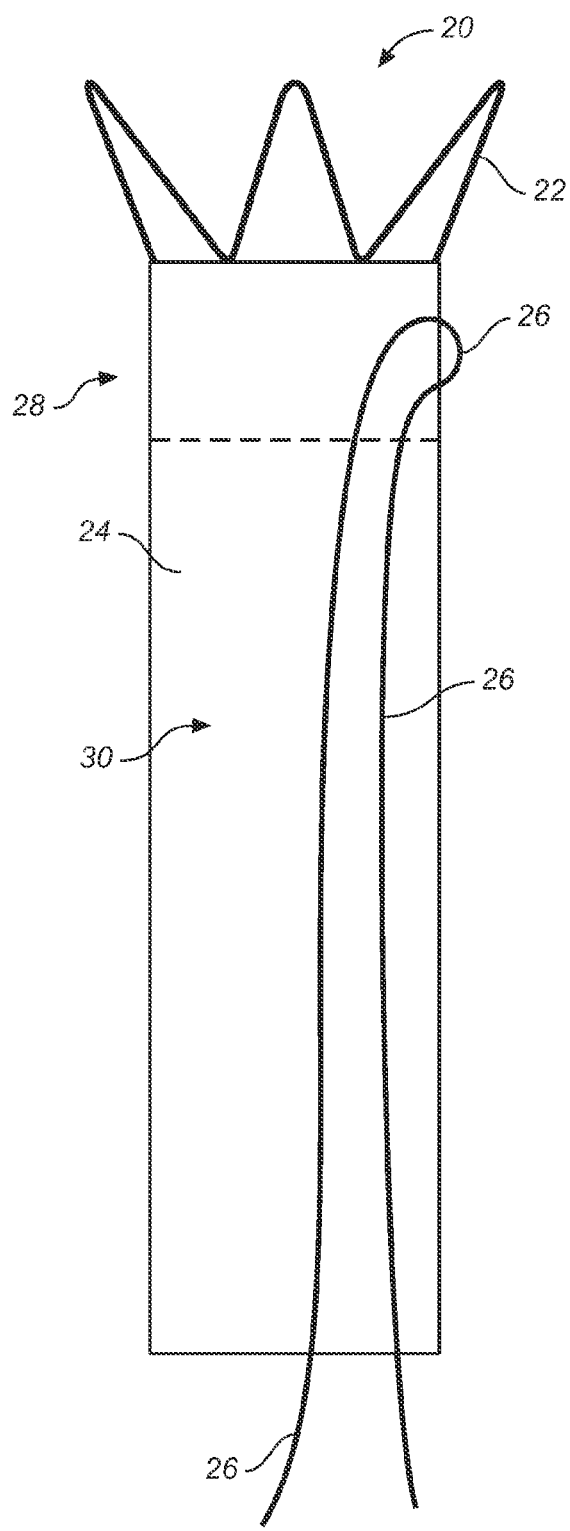
Figure 1C:
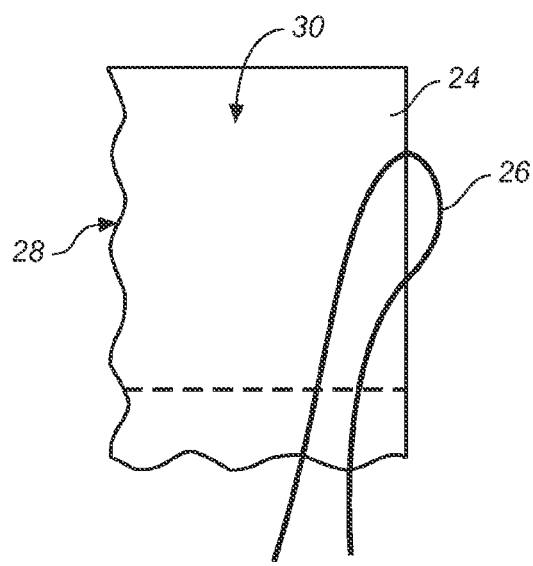

FIGS. 1A-1C, in which like elements share like reference numbers, are side, cross section, and detailed cross section views, respectively, of a stent graft. The stent graft 20, illustrated in the deployed state, includes a stent 22, graft material 24 supported by the stent 22, and a guide suture 26 joined to the graft material 24. The graft material 24 has a fixation region 28 and the guide suture 26 is joined to the graft material 24 in the fixation region 28. As used herein, the fixation region is defined as the region of the graft material where the fastener is to be attached. The guide suture 26 allows the stent graft 20 to direct a fixation tool head to a fixation point in a body lumen of a patient, so that the stent graft 20 can be fixed to the vessel wall. The length of the guide suture 26 is selected to extend from the fixation point in the body lumen to the outside of the body lumen. The stent graft 20 is deployed in the body lumen with one end of the guide suture 26 remaining outside. The physician can install a fixture tool head over the guide suture 26, advance the fixture tool head to the fixation point in the body lumen, and fix the graft material 24 to the body lumen wall with a fastener. The guide suture 26 can then be removed from the patient by pulling on the portion of the guide suture 26 outside of the body lumen (along a stent graft delivery path defined by the previously delivered stent graft). The guide suture 26 allows accurate placement of the fastener, which fixes and seals the graft material 24 to the body lumen wall.

The guide suture 26 can follow an in-out-in pattern through the graft material 24 to allow the guide suture 26 to be pulled from the body lumen after the fastener is attached to the body lumen wall. Referring to FIG. 1C, the graft material 24 forms a graft lumen 30. In this example, the guide suture 26 is a double-ended guide suture that follows a continuous path from the graft lumen 30 through the graft material 24 to the outside of the stent graft 20 and back through the graft material 24 into the graft lumen 30. As used herein, a double-ended guide suture is defined as a guide suture in which both ends of the guide suture extend outside the body lumen of the patient when the stent graft is deployed. The continuous path allows the physician to remove the guide suture 26 after the fastener is in place by pulling on one of the two ends of the guide suture 26 which remain outside the patient. The guide suture 26 slides through the graft material 24 until the trailing end of the guide suture 26 clears the graft material 24 and the guide suture 26 can be pulled from the graft lumen 30.

The stent graft 20 can be a straight or bifurcated stent graft. The stent 22 and the graft material 24 can be any stent and the graft material typically used for stent grafts. The stent can be self-expanding or balloon expandable, and can be a single unit along the whole length of the stent graft or a series of individual stents as illustrated in FIG. 1A. The stent can be made of can be made of spring steel, stainless steel, titanium, nickel titanium alloys (Nitinol), a polymer or copolymer, a combination of these materials, or other suitable materials. The stent 22 holds the graft material 24 against the body lumen wall when fixing the graft material 24 to the body lumen wall. Because the stent 22 is only required to holds the graft material 24 against the body lumen wall until the fasteners can be deployed, the stent 22 only needs to apply a limited force on the graft material 24. In one embodiment, the stent 22 is a thin spring interwoven with the graft material 24 in the fixation zone 28. In another embodiment, the stent 22 is a thin spring sutured to the graft material 24 in the fixation zone 28. A thin spring allows the stent graft 20 to be packed to a small diameter in the compressed state, reducing the size of catheter required to deliver the compressed stent graft to the deployment site.

The graft material can be any woven or interlocked graft material suitable for stent grafts, such as woven polymer materials, e.g., Dacron, or polytetrafluoroethylene (PTFE), or interlocked graft materials including knit, stretch, and velour materials. The guide suture can be made of the same materials as the graft material, as a braided, twisted, or drawn fiber, or metal wires, such as stainless steel or nitinol wires.

Figure 8A:
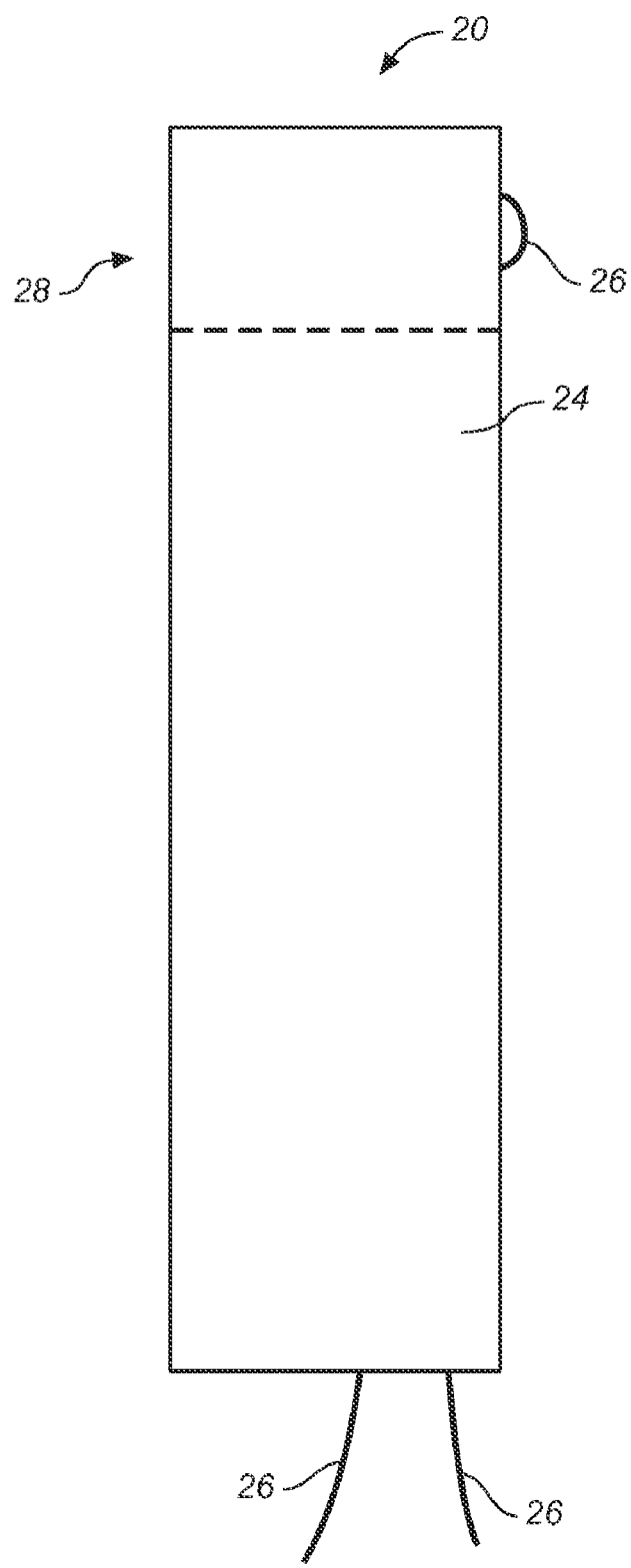
FIGS. 8A-8B are side and cross section views, respectively, of another embodiment of a stent graft in accordance with the present invention.
Figure 8B:
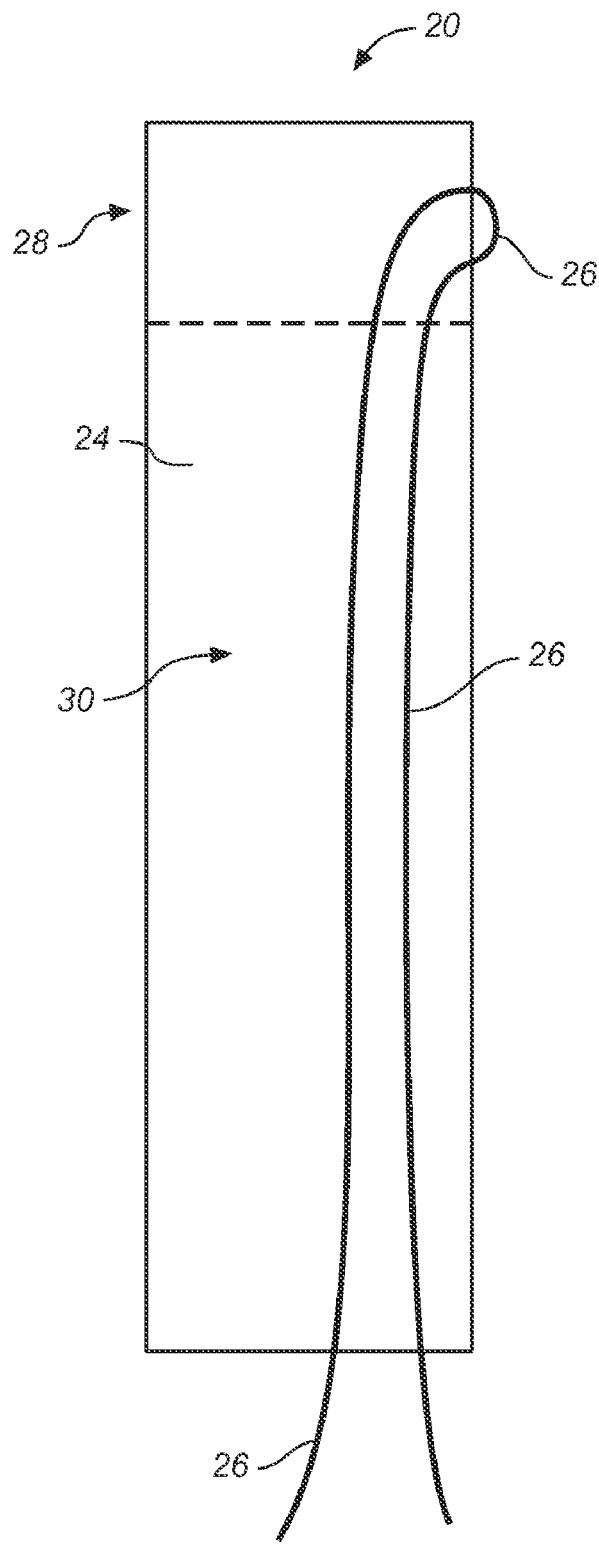

FIGS. 8A-8B, in which like elements share like reference numbers with each other and with FIGS. 1A-1C, are side and cross section views, respectively, of another embodiment of a stent graft. In this embodiment, the stent is integral to the graft material 24: no different material and/or structure is required. As defined herein, the stent is integral to the graft material when the graft material is self-supporting. The graft material of the stent graft 20 itself holds the graft material 24 against the body lumen wall when fixing the graft material 24 to the body lumen wall, functioning as the stent. In one embodiment, the graft material 24 is thicker in the fixation region 28 and the stent is the additional thickness of the graft material 24 without any other structure being required.

Figure 2A:
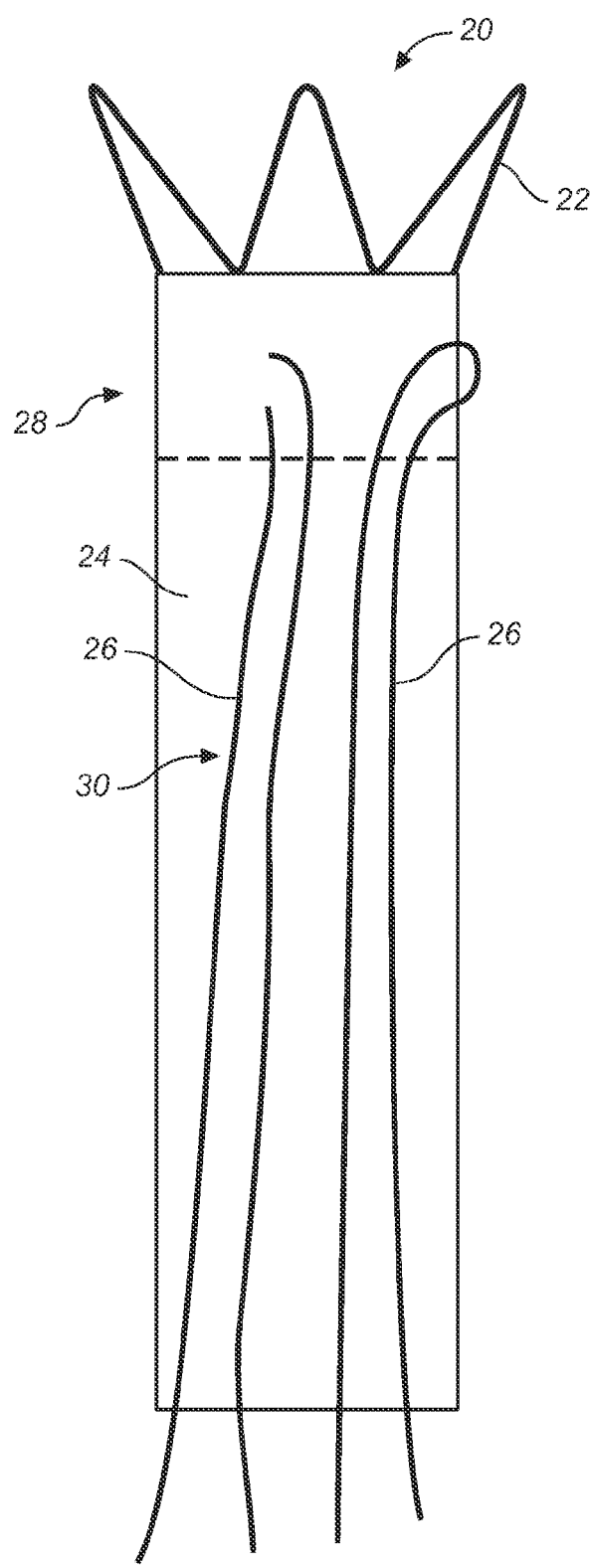
FIGS. 2A-2B are cross section views of another embodiment of a stent graft in accordance with the present invention.
Figure 2B:
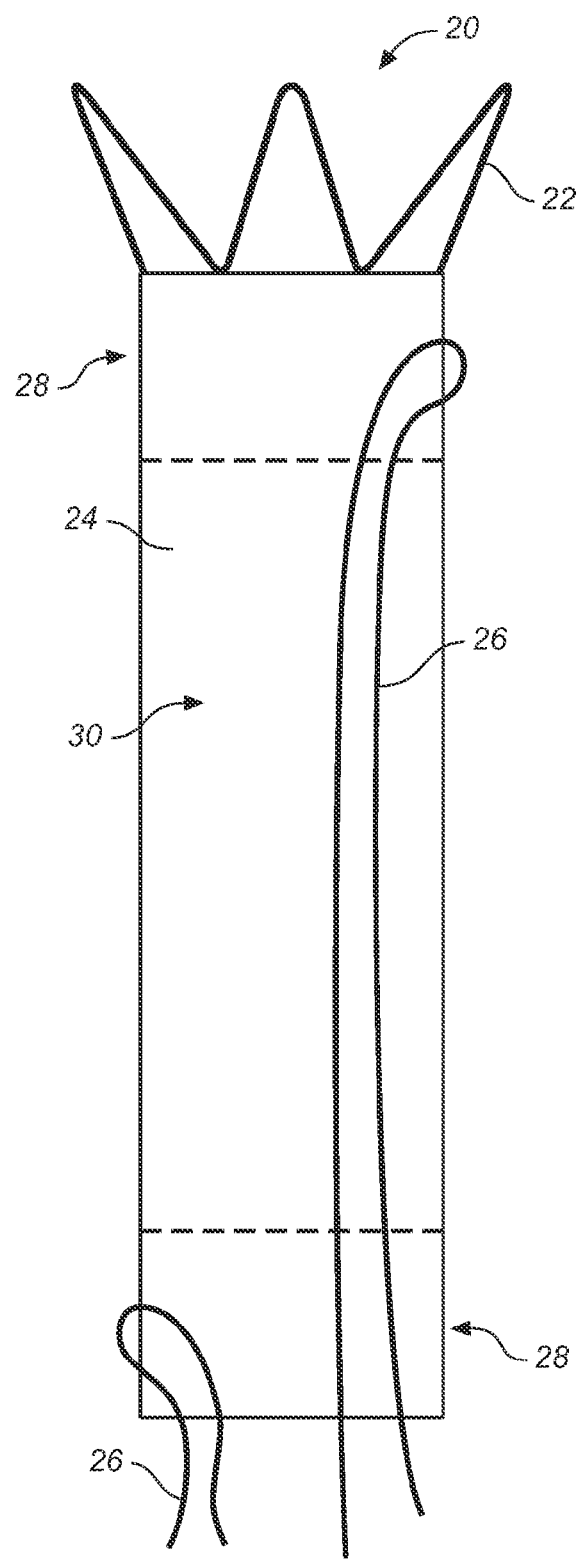

FIGS. 2A-2B, in which like elements share like reference numbers with each other and with FIGS. 1A-1C, are cross section views of another embodiment of a stent graft. FIG. 2A illustrates a stent graft 20 with two guide sutures 26 joined to the graft material 24 in the fixation region 28. FIG. 2B illustrates a stent graft 20 with two guide sutures 26 joined to the graft material 24 in two fixation regions 28. A number of guide sutures can be used when more than one fastener is to be inserted at more than one fixation point in the body lumen. Those skilled in the art will appreciate that the guide sutures 26 can be joined to the graft material 24 in any pattern desired to achieve any pattern of fasteners desired. When multiple fasteners are used to provide a better seal, the fasteners can be located close enough together to maintain the graft material 24 against the body lumen wall and prevent bypass flow paths from forming between the graft material 24 and the body lumen wall. A method of using multiple guide sutures to install multiple fasteners without repeated instrument exchange of the fixation tool is discussed below.

Figure 3A:
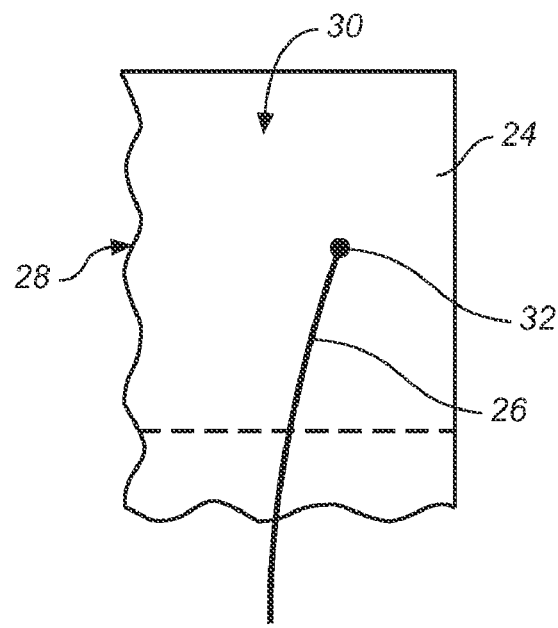
FIGS. 3A-3B are detailed cross section views of another embodiment of a stent graft in accordance with the present invention.
Figure 3B:
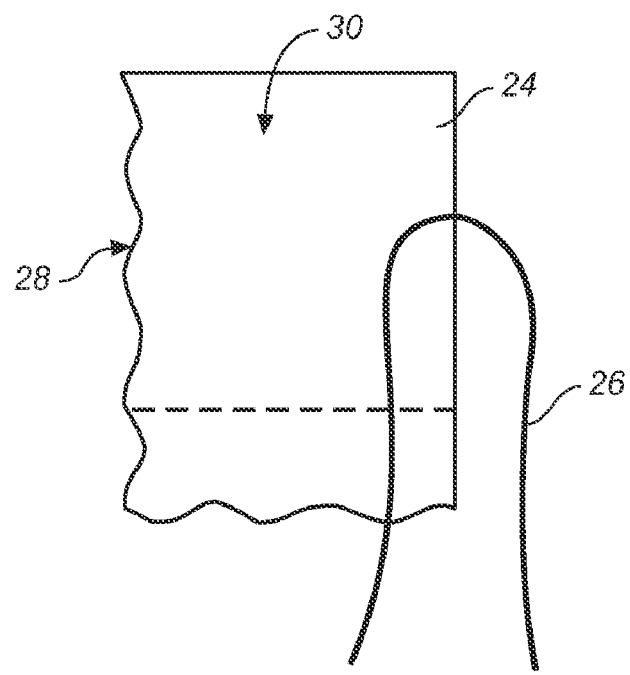

FIGS. 3A-3B, in which like elements share like reference numbers with each other and with FIGS. 1A-1C, are detailed cross section views of another embodiment of a stent graft. FIG. 3A illustrates an anchored guide suture 26, which has one end 32 anchored to the graft material 24 in the fixation region 28. As used herein, an anchored guide suture is defined as a guide suture in which one end of the guide suture is anchored to the graft material and the other end of the guide suture extends outside the body lumen of the patient when the stent graft is deployed. In one embodiment, the end 32 is glued to the graft material 24. In another embodiment, the end 32 is tied to the graft material 24. In yet another embodiment, the end 32 is tied and glued to the graft material 24. After the fastener is installed, the end 32 can be cut with a cutter on the fixation tool head or a separate cutting tool and the guide suture 26 pulled from the graft lumen 30. FIG. 3B illustrates a guide suture 26 following an in-out pattern through the graft material 24. The guide suture 26 follows a continuous path from the graft lumen 30 through the graft material 24 to the outside of the stent graft 20 and continues along the outside of the stent graft 20 along the body lumen wall. The continuous path allows the physician to remove the guide suture 26 after the fastener is in place by pulling on one of the two ends of the guide suture 26 which remain outside the patient. The guide suture 26 slides through the graft material 24 until the trailing end of the guide suture 26 clears the graft material 24 and the guide suture 26 can be pulled from the graft lumen 30.

Figure 4A:
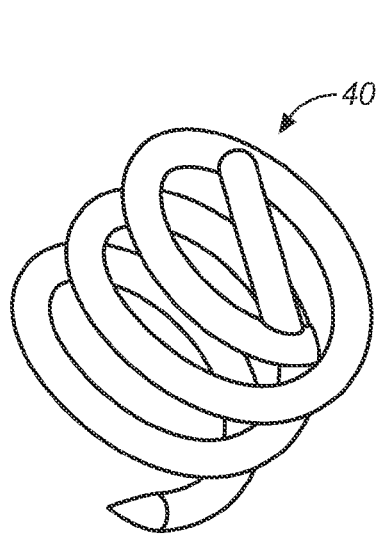
FIGS. 4A-4D are perspective views of fasteners for use with a stent graft in accordance with the present invention.
Figure 4B:
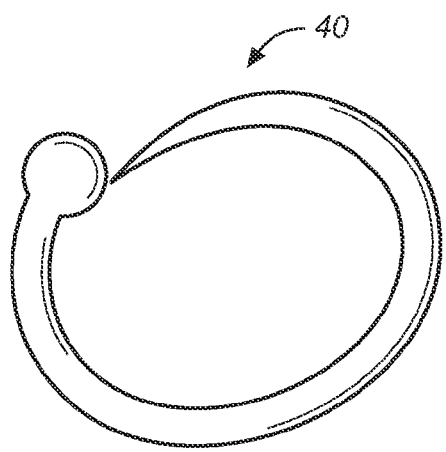
Figure 4C:
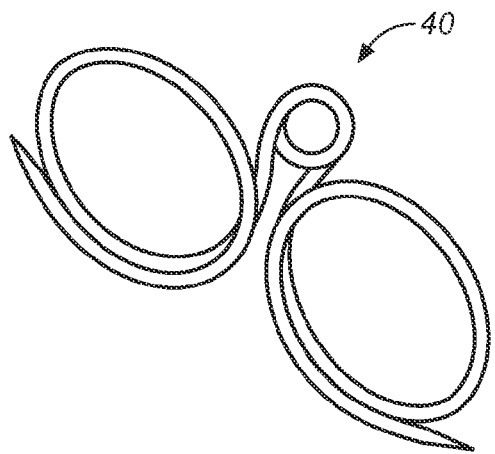
Figure 4D:
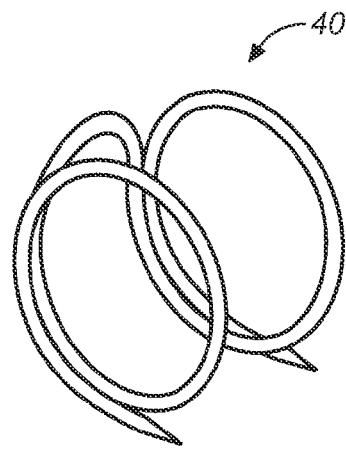

FIGS. 4A-4D are perspective views of fasteners for use with a stent graft. The fasteners are illustrated in the deployed state, i.e., the state employed to fix the graft material of the stent graft to the body lumen wall. Referring to FIG. 4A, the fastener 40 is a helical fastener and can be screwed through the graft material of the stent graft into the body lumen wall. The fastener 40 can be preformed in the helical shape or can be delivered as a straight wire that relaxes into the helical shape as the wire is deployed from the fixation tool. Referring to FIG. 4B, the fastener 40 is a coil fastener. The fastener 40 can be delivered as a straight wire of shape memory material that engages the graft material and the body lumen wall as the wire is deployed from the fixation tool. Referring to FIG. 4C, the fastener 40 is a planar staple. The fastener 40 made of shape memory material can be delivered in a staple shape, with two parallel legs 44 connected by a bridge 42. The legs 44 relax into the coil shape illustrated when the fastener 40 is deployed from the fixation tool, with the planes of the coils lying in one plane and wrapping in opposite directions. Referring to FIG. 4D, the fastener 40 is a ring staple. The fastener 40 made of shape memory material can be delivered in a staple shape, with two parallel legs 44 connected by a bridge 40. The legs 44 relax into the coil shape illustrated when the fastener 40 is deployed from the fixation tool, with the planes of the coils being parallel to each other and wrapping in the same direction. Those skilled in the art will appreciate that the fastener can be any fastener deliverable through a body lumen and capable of engaging the graft material of a stent graft and a body lumen wall.

FIGS. 5A-5C, in which like elements share like reference numbers, are top, detailed front, and detailed bottom views, respectively, of a fixation tool for use with a stent graft. The fixation tool follows the guide suture of the stent graft to the fixation point in the body lumen of a patient and deploys a fastener to fix the graft material of the stent graft to the body lumen wall.

Referring to FIG. 5A, the fixation tool 50 includes a handle 52, a tube 54, and a fixation tool head 56. The fixation tool 50 can be advanced through a catheter (not shown) until the fixation tool head 56 is at a fixation point where a fastener is to be deployed. The operator controls the deployment of a fastener from the fixation tool head 56 by manipulating controls 53 at the handle 52. In one embodiment, the fixation tool 50 holds a single fastener for deployment. In another embodiment, the fixation tool 50 holds a number of fasteners that can be delivered one at a time from the fixation tool head 56 without withdrawing the fixation tool 50 from the catheter.

The fixation tool can include visual indicators and/or radiopaque markers to indicate the rotational orientation of the fixation tool for the operator. In one embodiment, a visual indicator on the handle 52 indicates the direction in which the fastener will be deployed from the fixation tool head 56. In one embodiment, a radiopaque marker on the fixation tool head 56 indicates the direction in which the fastener will be deployed from the fixation tool head 56, so the operator can verify that the fastener will be deployed toward the body lumen wall. One such radiopaque marker is in the shape of the capital letter E with the arms of the letter indicating the direction that the body lumen wall should be for fixation.

Referring to FIGS. 5B and 5C, the end face 58 of the fixation tool head 56 includes a deployment aperture 60 and a guide aperture 62. Fasteners exit the deployment aperture 60 to engage the graft material and the body lumen wall. The guide aperture 62 continues through the fixation tool head 56 to the bottom face 64 of the fixation tool head 56. The suture guide joined to the graft material of the stent graft passes through the guide aperture 62 to guide the fixation tool head 56 to the fixation point. In one embodiment, the guide aperture 62 is sized to receive one guide suture. In another embodiment, the guide aperture 62 is sized to receive a number of guide sutures. In one embodiment, the edges of the guide aperture 62 are chamfered to allow smooth passage of the guide suture.

The fixation tool head 56 can also include a cutter 57 (illustrated by dashed lines) operable from the handle 52 to cut the guide suture after the fastener had been deployed. When the guide suture is anchored to the graft material, the guide suture is cut with the cutter so that the guide suture can be removed from the body lumen and the patient. In one embodiment, the cutter employs a single blade and shears the suture guide against the wall of the guide aperture 62. In another embodiment, the cutter employs double blades to scissor the suture guide. The cutter 57 can be slidable across the guide aperture 62 and actuated by a cable 55 (illustrated by dashed lines) between the handle 52 and the fixation tool head 56.

Those skilled in the art will appreciate that the fixation tool 50 is but a single example of the fixation tools that can be used with the stent graft of the present invention. The fixation tool can be any tool for fixing a fastener through graft material at a fixation point in a body lumen, with the tool delivering the fastener intraluminally and the deployment of the fastener being controlled from outside the patient. Particular features, such as the location of the guide aperture on the fixation tool head and the relative positions of the guide aperture and the deployment aperture depend on the type of fastener used. For example, the deployment aperture can be on the end face or the bottom face of the fixation tool head. In another example, the guide aperture can open through the top, bottom, and/or end face of the fixation tool head. The guide aperture is located to position the fastener at the fixation point while avoiding entanglement with the fattener or the mechanism of the fixation tool advancing the fastener. The guide aperture is not limited to the body of the fixation tool head and can be part of a structure built out from or attached to the fixation tool head.

FIGS. 6A-6F, in which like elements share like reference numbers with each other and with FIGS. 1-5, are schematic diagrams of fixation of a stent graft. The fixation tool head of a fixation tool is guided with a guide suture joined to the graft material of a stent graft to a fixation point in a body lumen of a patient, where the graft material can be fastened to the body lumen wall. The guide suture can then be detached from the graft material and retrieved from the body lumen. Although the guide suture 26 is illustrated with one end passing through the guide aperture 62 and the other end in the graft lumen 30, those skilled in that art will appreciate that both ends of the guide aperture 62 can pass through the guide aperture 62 as desired.

Figure 6A:
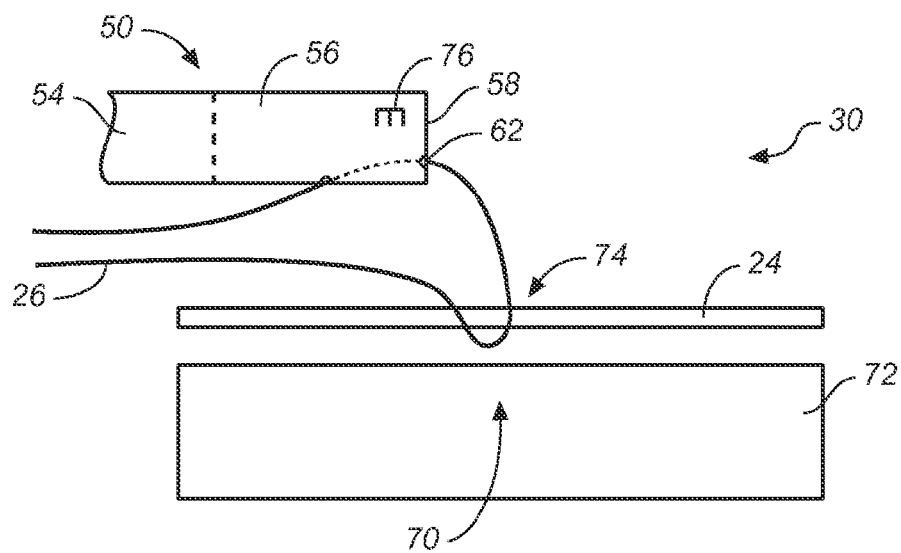
FIGS. 6A-6F are schematic diagrams of fixation of a stent graft in accordance with the present invention.

Referring to FIG. 6A, the stent graft has been deployed in a body lumen, so that the graft material 24 of the stent graft is adjacent to the fixation point 70 of the body lumen wall 72. For example, the fixation region of the stent graft can be deployed upstream of an abdominal aortic aneurysm. The stent graft can be deployed by advancing a guidewire through a body lumen, advancing a catheter containing the stent graft in a collapsed state through the body lumen over the guidewire, and releasing the stent graft into the body lumen at the deployment site. The guide suture 26 is joined to the graft material 24 and the joining point 74, i.e., the point at which the guide suture 26 joins the graft material 24, is aligned with the fixation point 70. The guide suture 26 extends from the joining point 74 to outside of the body lumen, outside of the patient. The guide suture 26 is threaded through the guide aperture 62 of the fixation tool head 56 while the fixation tool head 56 is outside of the patient. The fixation tool head 56 is then guided along the guide suture 26 through the body lumen to a point near the fixation point 70.

Figure 6B:
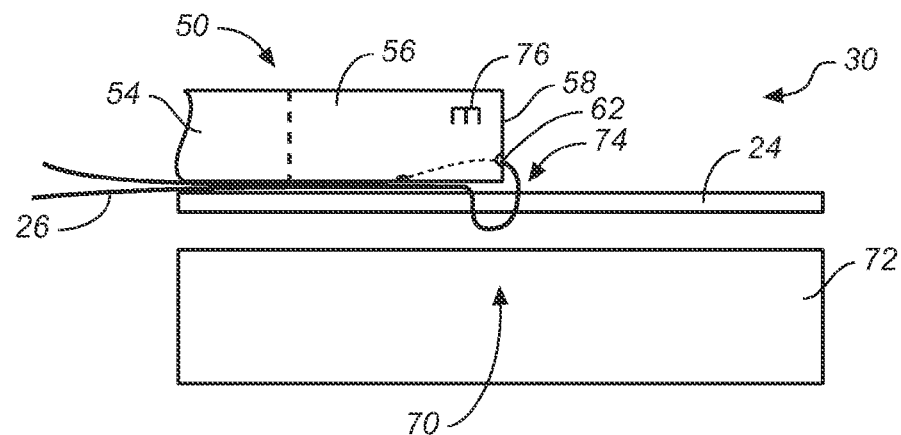

Referring to FIG. 6B, the fixation tool head 56 is advanced further along the guide suture 26 until the guide aperture 62 in the front face 58 of the fixation tool head 56 is at the joining point 74. The operator can maintain sufficient tension on the guide suture 26 to allow the fixation tool head 56 to follow the guide suture 26, without applying so much tension that the guide suture 26 pulls the graft material 24 too far away from the fixation point 70. The graft material 24 can be urged toward the fixation point 70 with the fixation tool head 56. The rotational orientation of the fixation tool head 56 can be verified fluoroscopically by checking the orientation of the radiopaque marker 76.

Figure 6C:
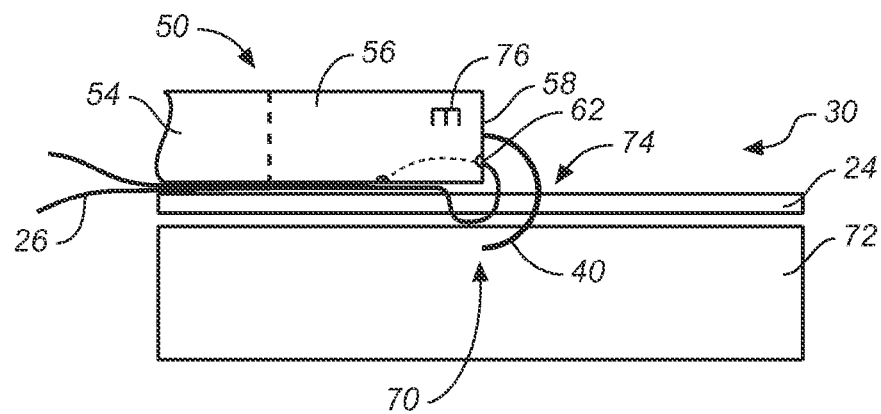

Referring to FIG. 6C, the fastener 40 is deployed from the fixation tool head 56 to fasten the graft material 24 to the body lumen wall 72 at the fixation point 70. In this example, the fastener 40 is a coil fastener or ring staple as illustrated in FIGS. 4B and 4D, respectively. The fastener 40 emerges from the front face 58 of the fixation tool head 56 under operator control and curls downward, passing through the graft material 24 and into the body lumen wall 72.

Figure 6D:
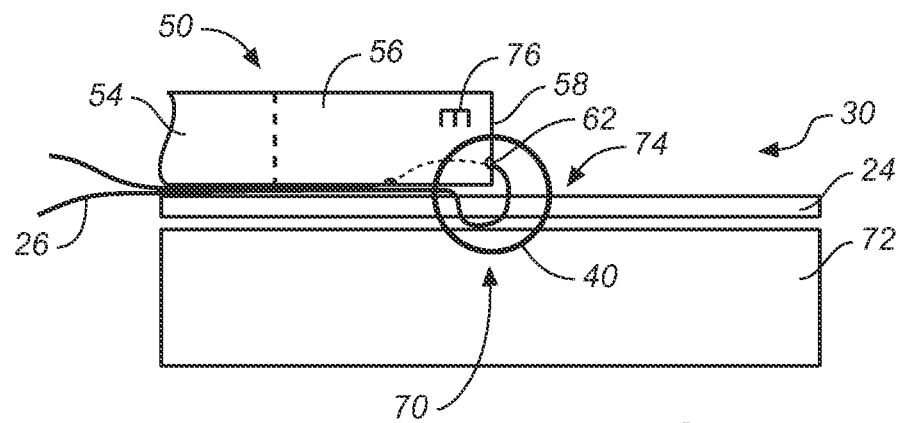
Figure 6E:
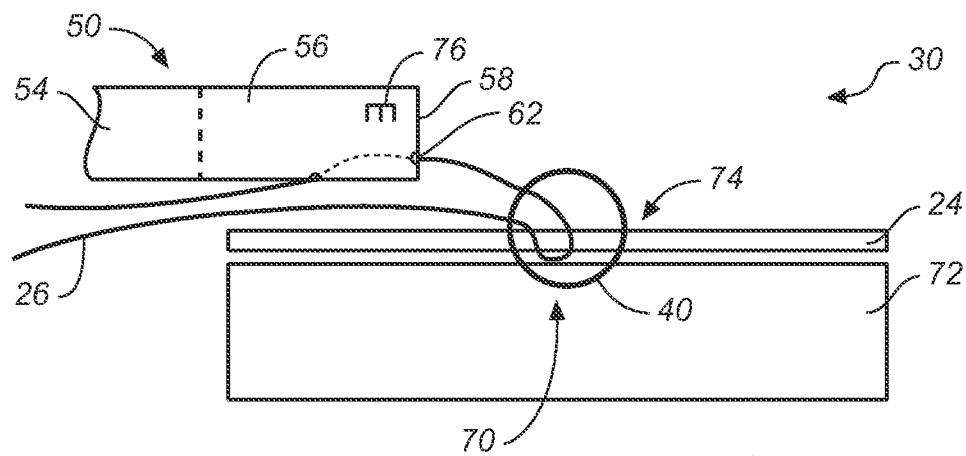

Referring to FIG. 6D, the fastener 40 continues to curl through the body lumen wall 72, passes through the graft material 24 again, and completes a circle, fastening the graft material 24 to the body lumen wall 72. Referring to FIG. 6E, the fixation tool head 56 is moved back from the fixation point 70.

Figure 6F:
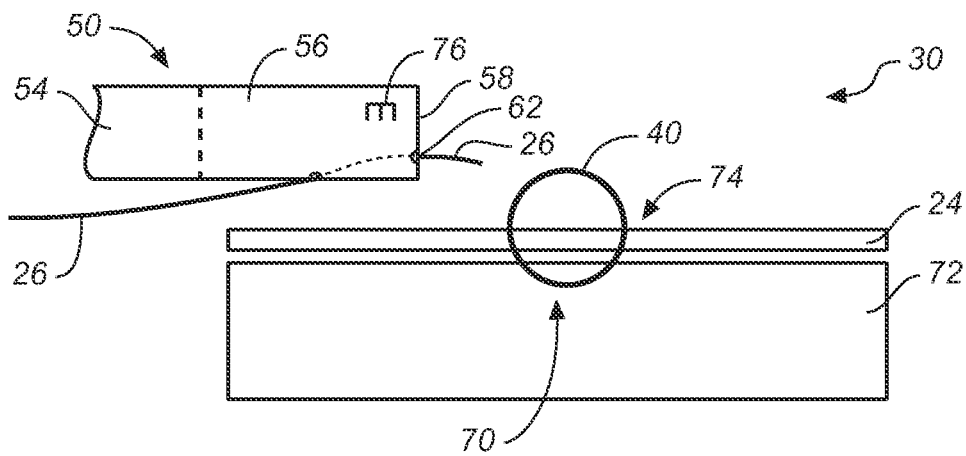

Referring to FIG. 6F, the operator pulls one end of the guide suture 26, so that the guide suture 26 slides through the guide aperture 62 of the fixation tool head 56 and becomes free of the graft material 24. The guide suture 26 and the fixation tool can then be withdrawn from the body lumen. In another embodiment, the guide suture 26 is anchored to the graft material 24 and the fixation tool head 56 includes a cutter that cuts the guide suture 26 near the joining point 74 under operator control.

Those skilled in the art will appreciate that the FIGS. 6A-6F illustrate one example of a method of fixation of a stent graft that can be modified as desired for a particular application. For example, any suitable fastener, such as a helical fastener, coil fastener, planar staple, ring staple, or other suitable type of fastener, can be used to fix the graft material to the body lumen wall. The particular geometry is affected by the type of fastener selected: the fastener can be deployed from the end, bottom, side, or top face of the fixation tool head; the guide aperture can follow a path from one face to the same face, or from one face to another. The particular combination is selected to avoid tangling the fastener with the guide suture or the guide aperture interfering with the fastener deployment. In another example, the guide suture can be joined to the graft material by following a continuous path through the graft material or by being anchored to the graft material.

FIGS. 7A-7E, in which like elements share like reference numbers with each other and with FIGS. 1-6, are schematic diagrams of fixation of a multi-guide suture stent graft. The stent graft has more than one guide suture that can be passed through the fixation tool head to allow fasteners to be placed at a number of fixation points in the body lumen wall.

Figure 7A:
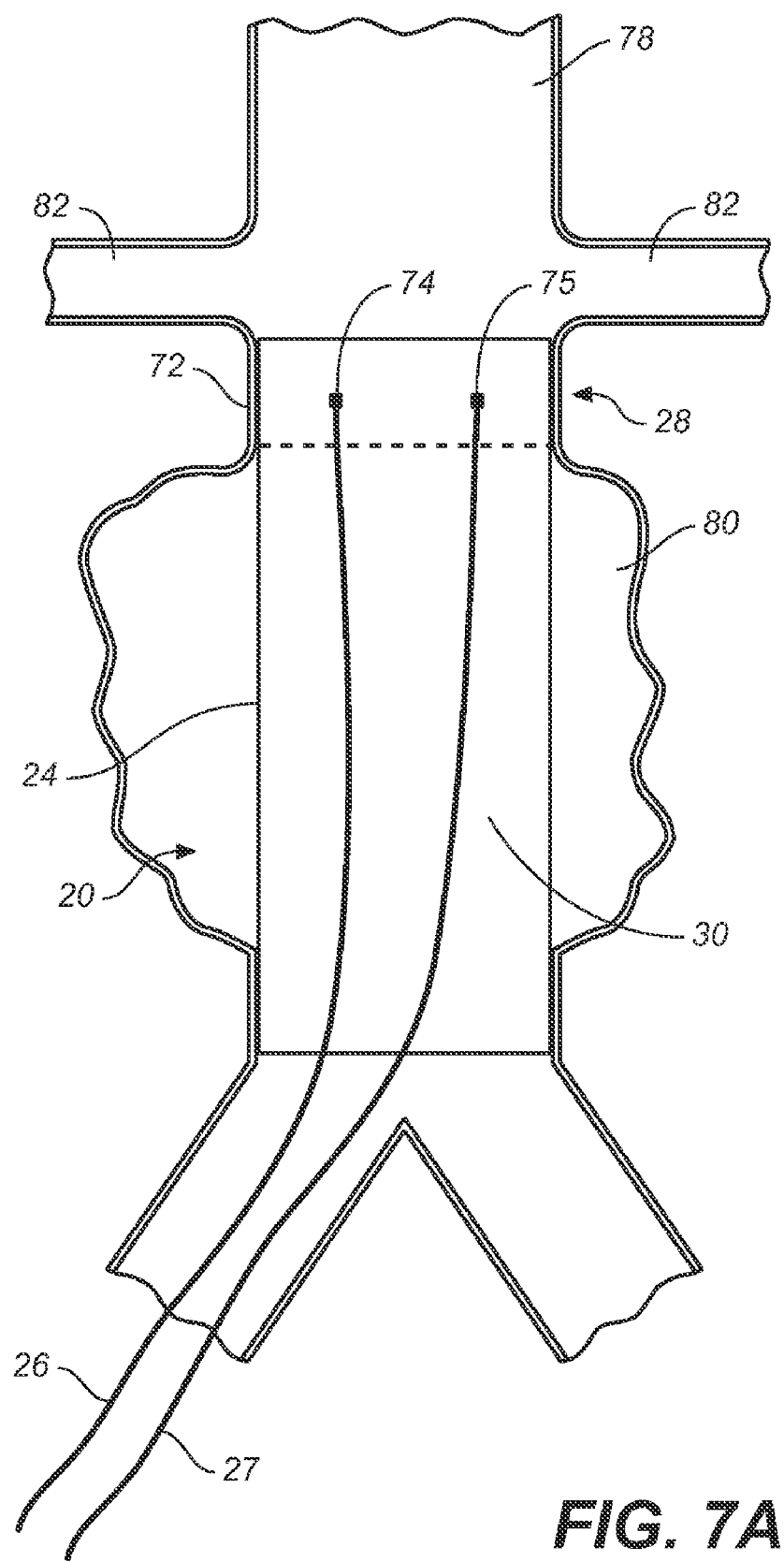
FIGS. 7A-7E are schematic diagrams of fixation of a multi-guide suture stent graft in accordance with the present invention.

Referring to FIG. 7A, the stent graft 20 has been deployed in a body lumen 78, so that the fixation region 28 of the stent graft 20 is against the body lumen wall 72. The stent graft 20 is illustrated in cross section so that the guide sutures 26, 27 and graft lumen 30 are visible. In this example, the stent graft 20 is deployed across an abdominal aortic aneurysm 80 with the fixation region 28 downstream of the renal arteries 82. The stent graft 20 can be deployed by advancing a guidewire through the body lumen 78, advancing a catheter containing the stent graft 20 in a collapsed state through the body lumen 78 over the guidewire, and releasing the stent graft 20 into the body lumen 78 at the abdominal aortic aneurysm 80. The guide sutures 26, 27 are joined to the graft material 24 at joining points 74, 75. The sutures 26, 27 extend from the joining points 74, 75 to the outside of the patient. The catheter which would typically be around the guide sutures 26, 27 has been omitted from the figures for clarity of illustration. The catheter can be pulled back after the stent graft 20 has been deployed and then advanced into the graft lumen 30 by following the guide sutures 26, 27 to move the distal end of the catheter closer to the joining points 74, 75. This decreases the distance the fixation tool head must travel outside the catheter.

Figure 7B:
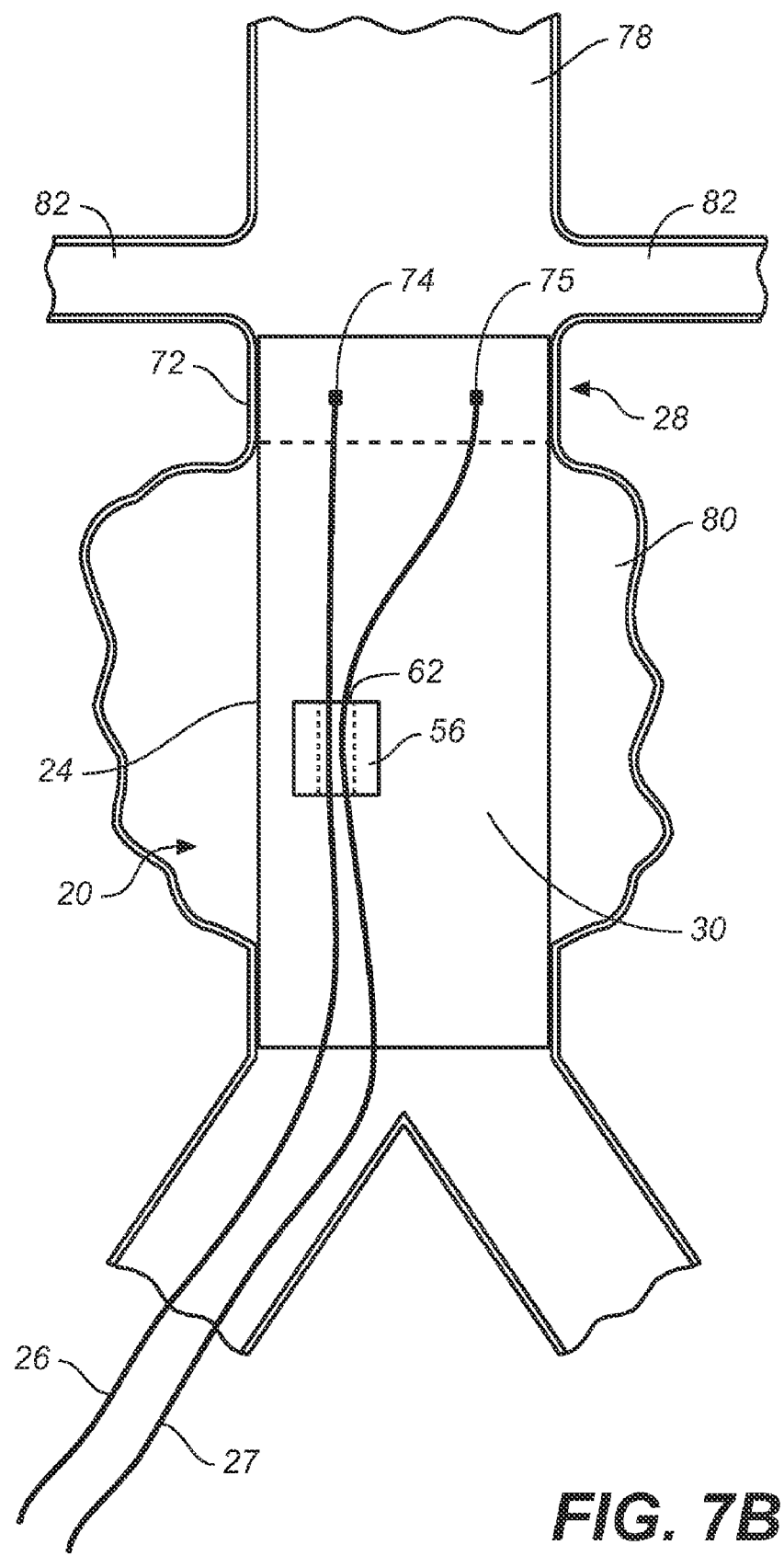

Referring to FIG. 7B, the guide sutures 26, 27 are threaded through the guide aperture 62 of the fixation tool head 56 while the fixation tool head 56 is outside of the patient. The fixation tool head 56 is then guided along the guide sutures 26, 27 into the graft lumen 30. The tube of the fixation tool which moves the fixation tool head 56 has been omitted from the figures for clarity of illustration.

Figure 7C:
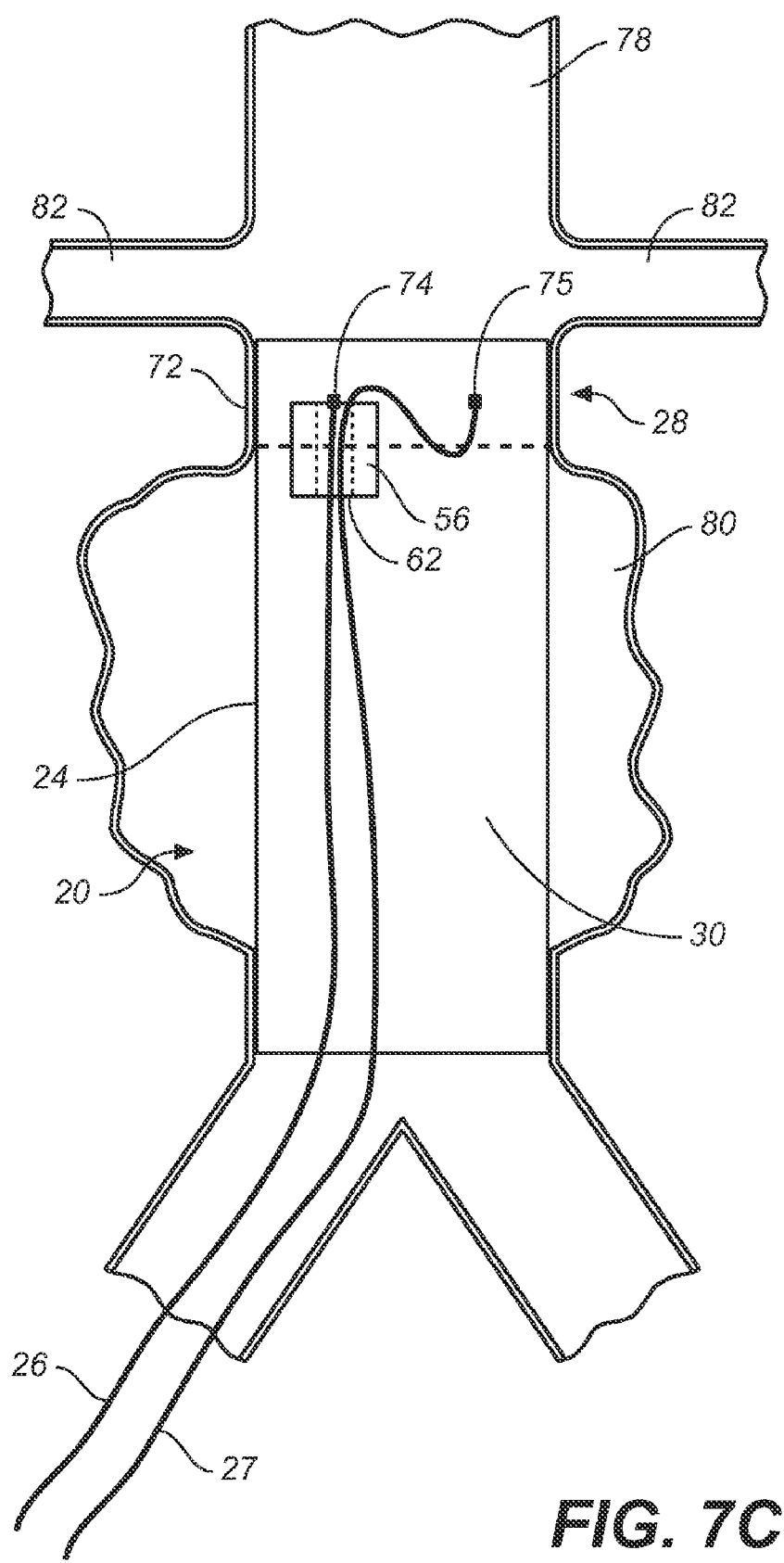

Referring to FIG. 7C, the fixation tool head 56 is guided along the guide suture 26 to reach the joining point 74, positioning the fixation tool head 56 where a fastener is to be deployed. The fixation tool 50 holds a number of fasteners that can be delivered one at a time from the fixation tool head 56 without withdrawing the fixation tool 50 from the graft lumen 30. The operator can maintain sufficient tension on the guide suture 26 to allow the fixation tool head 56 to follow the guide suture 26, without applying so much tension that the guide suture 26 pulls the graft material 24 too far away from the body lumen wall 72. The guide suture 27 can be slack, with only enough tension to avoid inadvertent entanglement. The graft material 24 can be urged toward the fixation point 70 with the fixation tool head 56. The rotational orientation of the fixation tool head 56 can be verified fluoroscopically. The fixation tool head 56 deploys a fastener to fasten the graft material 24 to the body lumen wall 72.

Figure 7D:
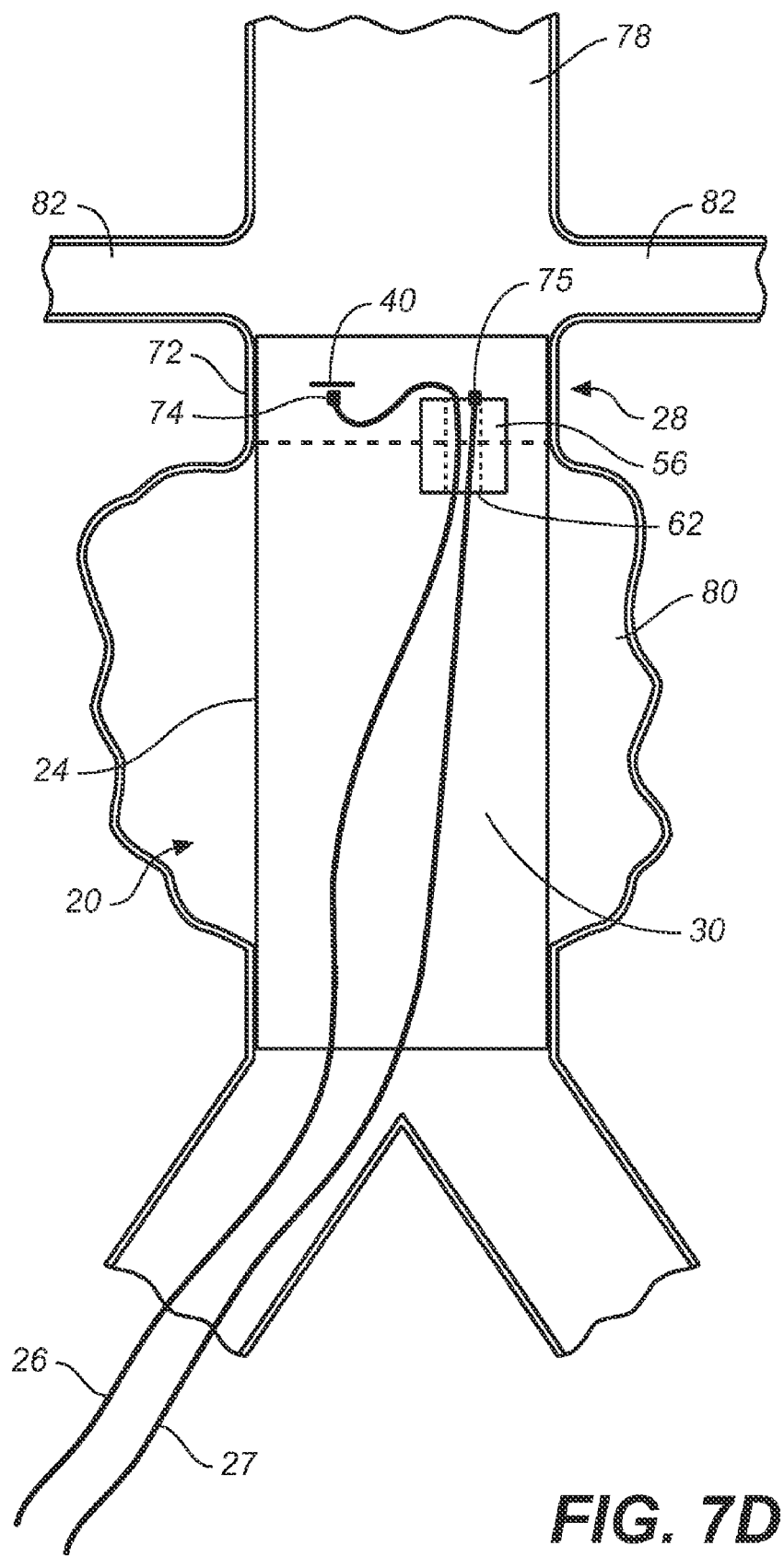

Referring to FIG. 7D, the fastener 40 is in place and the fixation tool head 56 has been moved to the joining point 75. The fixation tool head 56 can be located at the joining point 75 from the joining point 74 by withdrawing the fixation tool head 56 proximally from the joining point 74, slacking off tension on the guide suture 26, applying tension to the guide suture 27, and guiding the fixation tool head 56 along the guide suture 27 to the joining point 75. The fixation tool head 56 deploys another fastener to fasten the graft material 24 to the body lumen wall 72.

Figure 7E:
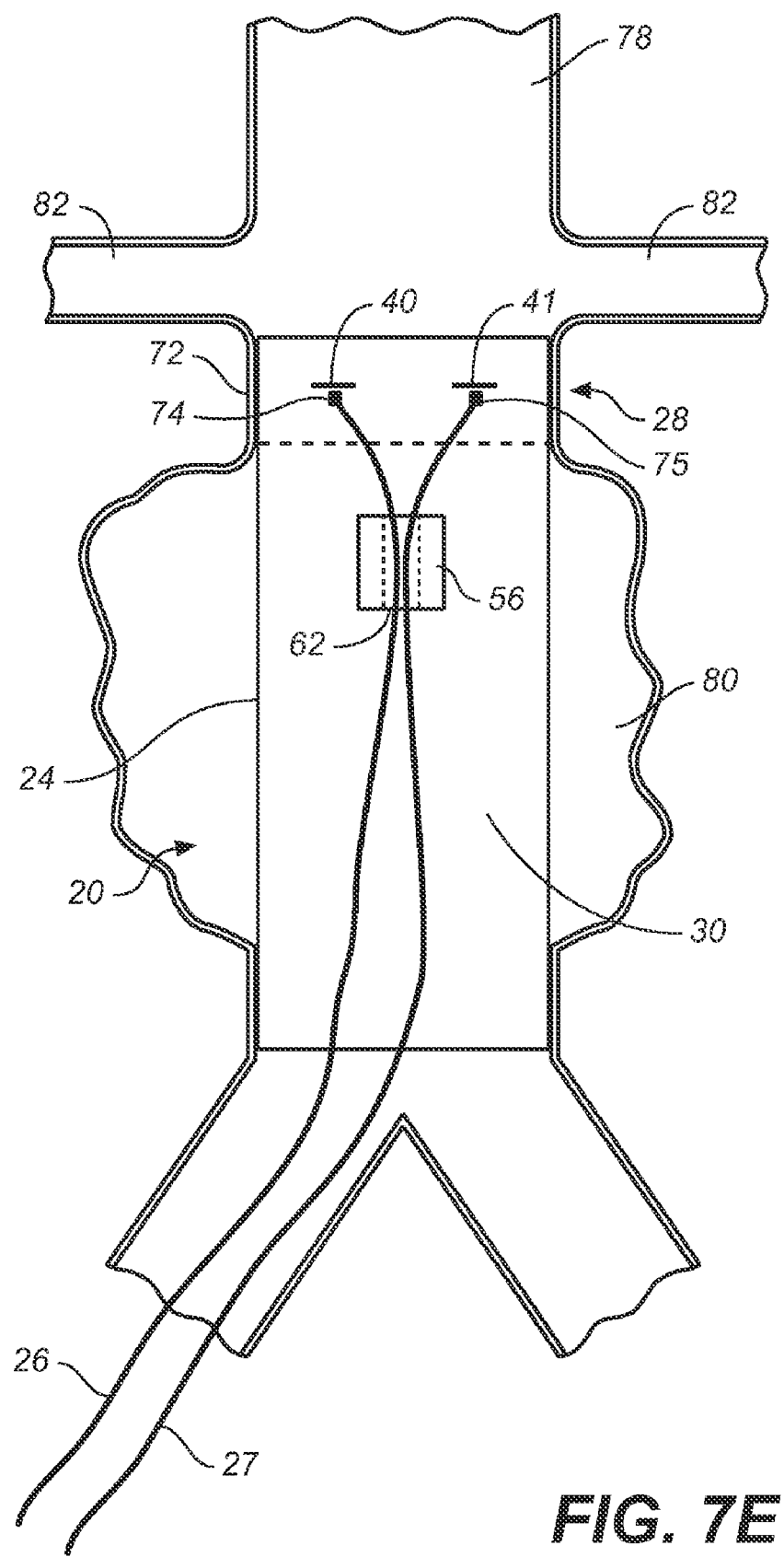

Referring to FIG. 7E, the second fastener 41 is in place and the fixation tool head 56 has been withdrawn proximally from the joining point 75. The guide sutures 26, 27 are can be removed from the graft material 24. When the guide sutures are double-ended guide sutures, the guide sutures 26, 27 can be removed by pulling one end of the guide suture. When the guide sutures are anchored guide sutures, the guide sutures 26, 27 can be removed by cutting the guide sutures 26, 27 near the joining points 74, 75 and pulling the guide sutures from the patient. Those skilled in the art will appreciate that any number of guide sutures can be used to fix the graft material to the body wall at any number of fixation points desired.

Figure 9:
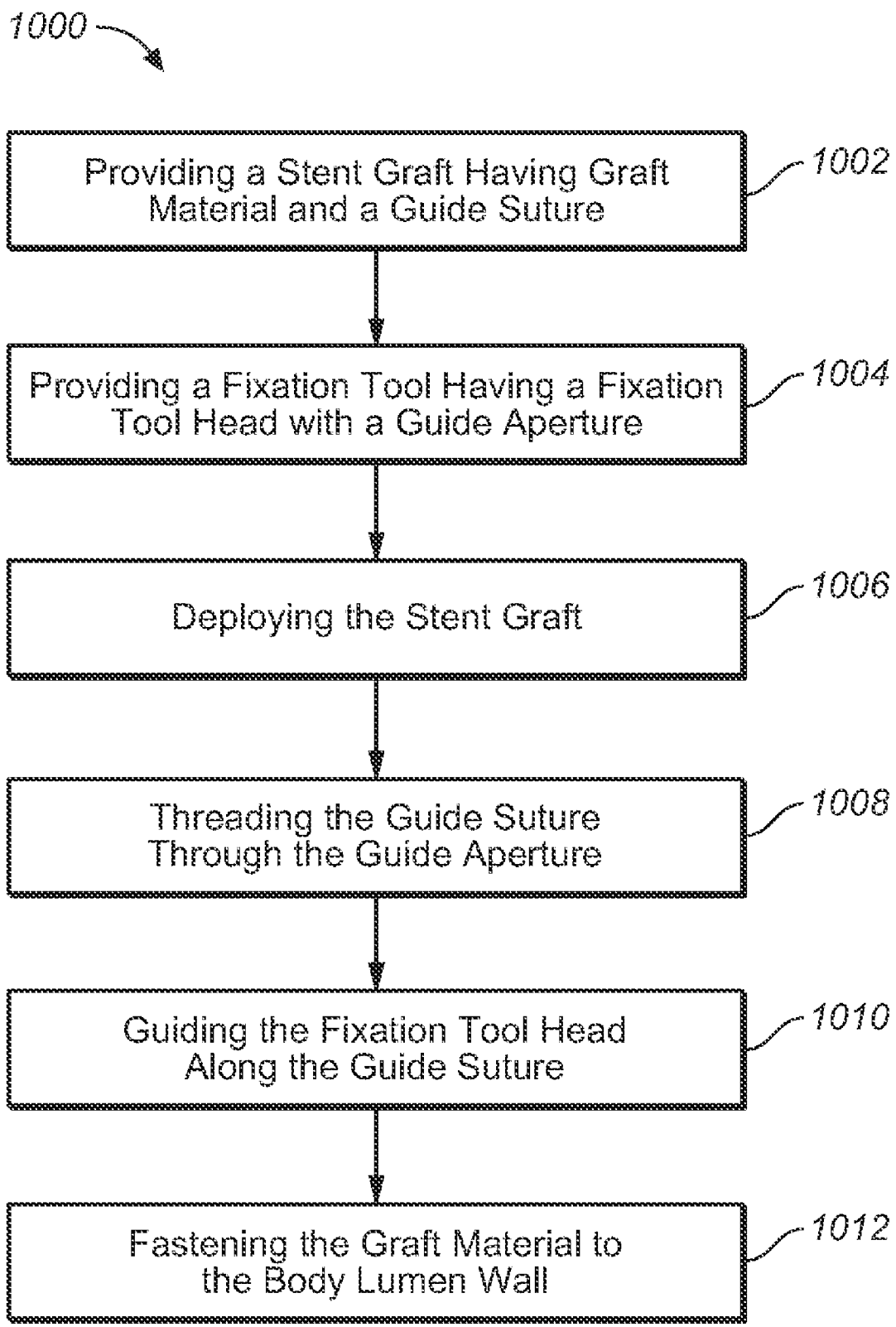
FIG. 9 is a flowchart of a method of fixing a stent graft to a body lumen wall in accordance with the present invention.

FIG. 9 is a flowchart of a method of s fixing a stent graft to a body lumen wall. The method 1000 includes providing a stent graft having graft material and a guide suture 1002, providing a fixation tool having a fixation tool head with a guide aperture 1004, deploying the stent graft 1006, threading the guide suture through the guide aperture 1008, guiding the fixation tool head along the guide suture 1010, and fastening the graft material to the body lumen wall 1012.

The providing a stent graft having graft material and a guide suture 1002 includes providing a stent graft having graft material and a guide suture joined to the graft material. The stent graft can include graft material disposed on and/or within a stent. In one embodiment, the stent is integral to the graft material. The stent can be any structure urging the graft material toward the body lumen wall sufficiently that the graft material can be fastened to the body lumen wall. The guide sutures are of sufficient length to extend from a fixation point in the body lumen to outside of the body lumen.

The providing a fixation tool having a fixation tool head with a guide aperture 1004 includes providing a fixation tool having a fixation tool head, the fixation tool head defining a guide aperture operable to receive the guide suture. The fixation tool delivers a fastener to the fixation point in the body lumen under operator control. The fastener is deployed from the fixation tool head. The guide aperture is sized to receive one or more guide sutures. In one embodiment, the fixation tool head also includes a cutter for cutting the guide suture once the graft material is fastened to the body lumen wall.

The deploying the stent graft 1006 includes deploying the stent graft in a body lumen. The stent graft can be deployed by advancing a guidewire through the body lumen, advancing a catheter containing the stent graft in a collapsed state through the body lumen over the guidewire, and releasing the stent graft into the body lumen at the deployment site. In another embodiment, a balloon expands the stent graft once the stent graft is outside the catheter.

The threading the guide suture through the guide aperture 1008 can be performed outside the patient before the fixation tool head is inserted in the body lumen. When a number of fasteners are to be installed, the guide suture for each of the fasteners is threaded through the guide aperture.

The guiding the fixation tool head along the guide suture 1010 includes guiding the fixation tool head along the guide suture to a fixation point. The operator can maintain sufficient tension on the guide suture to allow the fixation tool head to follow the guide suture, without applying so much tension that the guide suture pulls the graft material too far away from the fixation point. The tension on the guide suture can be released when the fixation tool head reaches the fixation point.

The fastening the graft material to the body lumen wall 1012 includes fastening the graft material to the body lumen wall at the fixation point. The fastening can include deploying a fastener from the fixation tool head to fix the graft material to the body lumen wall. The graft material can be urged toward the fixation point of the body lumen wall with the fixation tool head. The rotational orientation of the fixation tool head can be verified fluoroscopically. The fastener can be a helical fastener, coil fastener, planar staple, ring staple, or any other fastener suitable for fastening the graft material to the body lumen wall.

The method 1000 can continue with removing the guide suture. In one embodiment, the guide suture is a double-ended guide suture and removing the guide suture includes pulling the graft suture from the graft material, i.e., pulling one end of the guide suture so the guide suture passes through and comes free of the graft material. In another embodiment, the guide suture is an anchored guide suture and removing the guide suture includes cutting the graft suture with the fixation tool head, such as cutting the guide suture with a cutter in the fixation tool head. The cut guide suture can then be pulled from the body lumen.

The method 1000 can be used to install a number of fasteners without withdrawing the fixation tool head from the graft lumen. The stent graft further includes at least one additional guide suture joined to the graft material. The threading the guide suture through the guide aperture 1008 also includes threading the additional guide suture through the guide aperture with the initial guide suture. When the graft material has been fastened to the body lumen wall at the initial fixation point, the fixation tool head can be guided along the additional guide suture to an additional fixation point and the graft material fastened to the body lumen wall at the additional fixation point. The tension of the guide sutures can be varied to facilitate guiding the fixation tool head to each of the fixation points. The initial guide suture can be held in tension and the additional guide suture held slack when guiding the fixation tool head along the initial guide suture to the initial fixation point. The additional guide suture can be held in tension and the initial guide suture held slack when guiding the fixation tool head along the additional guide suture to the additional fixation point. The guide sutures can be pulled from the graft material together or separately, or can be cut simultaneously with a cutter in the fixation tool head.

While specific embodiments according to the invention are disclosed herein, various changes and modifications can be made without departing from the spirit and scope of the embodiments disclosed.

The invention claimed is:

1. A stent graft for fastening to a fixation point in a body lumen, the stent graft comprising:
   a stent;
   a graft material supported by the stent and having a fixation region; and
   a guide suture joined to the graft material in the fixation region, the guide suture having a length selected to extend from the fixation point to outside of the body lumen, the guide suture being joined to the graft material before the stent graft is deployed in the body lumen.

2. The stent graft of claim 1 wherein the stent is a thin spring interwoven with the graft material.

3. The stent graft of claim 1 wherein the stent is integral to the graft material.

4. The stent graft of claim 1 wherein the graft material forms a graft lumen and the guide suture is a double-ended guide suture joined to the graft material along a continuous path from the graft lumen through the graft material and back through the graft material into the graft lumen.

5. The stent graft of claim 1 wherein the graft material forms a graft lumen and the guide suture is a double-ended guide suture joined to the graft material along a continuous path from the graft lumen through the graft material and outside the stent graft.

6. The stent graft of claim 1 wherein one end of the guide suture is anchored to the graft material in the fixation region.

7. The stent graft of claim 6 wherein the one end is glued to the graft material.

8. The stent graft of claim 6 wherein the one end is tied to the graft material.

9. The stent graft of claim 1 further comprising a second guide suture joined to the graft material in the fixation region.

10. The stent graft of claim 1 wherein the graft material has a second fixation region and further comprising a second guide suture joined to the graft material in the second fixation region.

11. A stent graft fixation system comprising:
    a stent graft having graft material;
    a guide suture joined to the graft material, the guide suture being joined to the graft material before the stent graft is deployed in a body lumen; and
    a fixation tool having a fixation tool head, the fixation tool head defining a guide aperture operable to receive the guide suture.

12. The system of claim 11 wherein the stent graft further comprises a thin spring interwoven with the graft material.

13. The system of claim 11 wherein the graft material forms a graft lumen and the guide suture is a double-ended guide suture joined to the graft material along a continuous path from the graft lumen through the graft material and back through the graft material into the graft lumen.

14. The system of claim 11 wherein the graft material forms a graft lumen and the guide suture is a double-ended guide suture joined to the graft material along a continuous path from the graft lumen through the graft material and outside the stent graft.

15. The system of claim 11 wherein one end of the guide suture is anchored to the graft material.

16. The system of claim 11 further comprising a second guide suture joined to the graft material.

17. The system of claim 11 further comprising a cutter slidable across the guide aperture.

18. The system of claim 17 wherein the cutter is selected from the group consisting of a single blade cutter and double blade cutter.

19. The system of claim 11 further comprising a catheter operable to receive the stent graft in a compressed state.

20. The system of claim 11 further comprising a fastener deployable from the fixation tool head.

21. The system of claim 20 wherein the fastener is selected from the group consisting of a helical fastener, coil fastener, planar staple, and ring staple.

22. A method of fixing a stent graft to a body lumen wall, the method comprising:
    providing a stent graft having graft material and a guide suture joined to the graft material;
    providing a fixation tool having a fixation tool head, the fixation tool head defining a guide aperture operable to receive the guide suture;
    deploying the stent graft in a body lumen;
    threading the guide suture through the guide aperture;
    guiding the fixation tool head along the guide suture to a fixation point; and
    fastening the graft material to the body lumen wall at the fixation point.

23. The method of claim 22 wherein the fastening further comprises urging the graft material toward the fixation point of the body lumen wall with the fixation tool head.

24. The method of claim 22 wherein the fastening further comprises verifying rotational orientation of the fixation tool head fluoroscopically.

25. The method of claim 22 further comprising pulling the graft suture from the graft material.

26. The method of claim 22 further comprising cutting the graft suture with the fixation tool head.

27. The method of claim 22 wherein:
    the stent graft further comprises a second guide suture joined to the graft material;
    the threading further comprises threading the second guide suture through the guide aperture with the guide suture; and
    the method further comprises:
    guiding the fixation tool head along the second guide suture to a second fixation point; and
    fastening the graft material to the body lumen wall at the second fixation point.

28. A stent graft fixation system for stent graft fixation to a fixation point in a body lumen wall, the system comprising:
    a stent graft having graft material and a guide suture joined to the graft material, the guide suture being joined to the graft material before the stent graft is deployed in a body lumen;
    means for fastening the graft material to the body lumen wall;
    means for delivering the fastening means along the guide suture to the fixation point; and
    means for deploying the fastening means at the fixation point.

* * * * *